(12) United States Patent
Wells et al.

(10) Patent No.: US 6,207,955 B1
(45) Date of Patent: Mar. 27, 2001

(54) PNEUMATICALLY ASSISTED ELECTROSPRAY DEVICE WITH ALTERNATING PRESSURE GRADIENTS FOR MASS SPECTROMETRY

(75) Inventors: Gregory J. Wells, Fairfield; Roger C. Tong, Berkeley; Peter P. Yee, San Ramon, all of CA (US)

(73) Assignee: Varian, Inc., Palo Alto, CA (US)

( * ) Notice: Subject to any disclaimer, the term of this patent is extended or adjusted under 35 U.S.C. 154(b) by 0 days.

(21) Appl. No.: 09/162,261

(22) Filed: Sep. 28, 1998

(51) Int. Cl.[7] .............................. B01D 59/44; H01J 49/00
(52) U.S. Cl. ......................... 250/288; 250/281; 250/282
(58) Field of Search ................................... 250/288, 281, 250/282; 204/299

(56) References Cited

U.S. PATENT DOCUMENTS

| | | | |
|---|---|---|---|
| 4,861,988 | * 8/1989 | Henion et al. | 250/288 |
| 5,115,131 | * 5/1992 | Jorgenson et al. | 250/288 |
| 5,170,053 | * 12/1992 | Hail et al. | 250/288 |
| 5,306,412 | * 4/1994 | Whitehouse et al. | 204/299 |
| 5,349,186 | * 9/1994 | Ikonomu et al. | 250/288 |

FOREIGN PATENT DOCUMENTS

WO 97 28556   8/1997   (WO) .
WO 98 42007   9/1998   (WO) .

* cited by examiner

*Primary Examiner*—Teresa M. Arroyo
*Assistant Examiner*—Johnnie L. Smith, II
(74) *Attorney, Agent, or Firm*—Edward H. Berkowitz

(57) ABSTRACT

An apparatus for producing gas-phase ions from a sample compound in a carrier liquid. The electrospray needle (or capillary) of the present invention includes a central metal tube which carries the liquid containing the sample compound. The central tube is surrounded by a plurality of tubes which transport a nebulizing gas. The nebulizing gas tubes are placed symmetrically around the outside of the liquid containing tube. The nebulizer of the present invention produces a symmetric, non-annular gas flow which has variations in pressure around the circumference of the central tube. The pressure variations of the nebulizing gas flow produce additional shear forces on the liquid emerging from the central tube. This assists in forming a uniform electrospray of droplets from the liquid at lower nebulizing gas flow rates, thereby reducing the disadvantageous effects of the higher gas flow rates used in the art. The symmetric arrangement of the nebulizing gas tubes provides support for the central sample carrying tube, thereby reducing the alignment problems found in prior art devices, and enhancing uniformity of the electrospray.

12 Claims, 16 Drawing Sheets

Figure 1B:
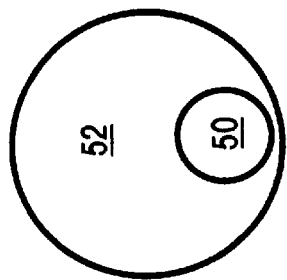

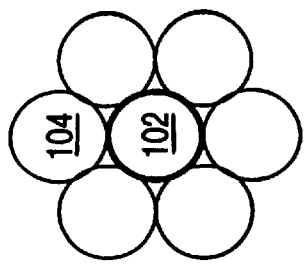
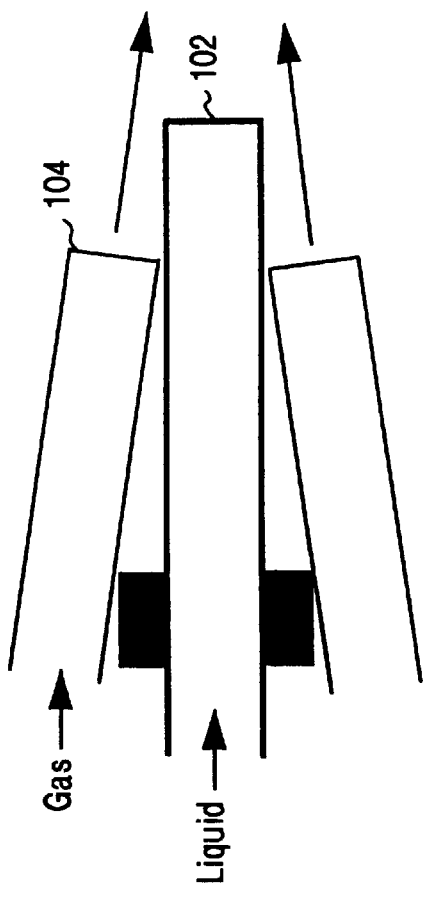
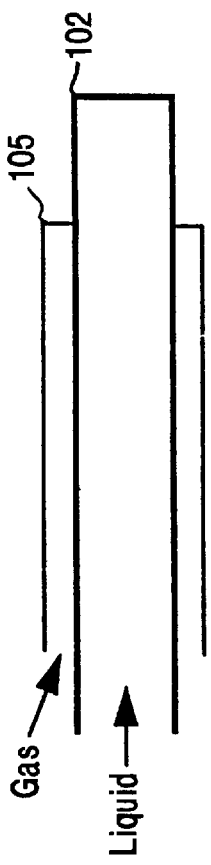

US 6,207,955 B1

PNEUMATICALLY ASSISTED ELECTROSPRAY DEVICE WITH ALTERNATING PRESSURE GRADIENTS FOR MASS SPECTROMETRY

FIELD OF THE INVENTION

The present invention relates to apparatus and methods for characterizing materials using mass spectrometry, and more specifically, to an improved electrospray device which can be used for introduction of liquid samples into a mass spectrometer.

BACKGROUND OF THE INVENTION

Mass spectrometers have become common tools in chemical analysis. Generally, mass spectrometers operate by separating ionized atoms or molecules based on differences in their mass-to-charge ratio (m/e). A variety of mass spectrometer devices are commonly in use, including ion traps, quadrupole mass filters, and magnetic sector.

The general stages in performing a mass-spectrometric analysis are:

(1) create gas-phase ions from a sample; (2) separate the ions in space or time based on their mass-to-charge ratio; and (3) measure the quantity of ions of each selected mass-to-charge ratio. Thus, in general, a mass spectrometer system consists of an ion source, a mass-selective analyzer, and an ion detector. In the mass-selective analyzer, magnetic and electric fields may be used, either separately or in combination, to separate the ions based on their mass-to-charge ratio. Hereinafter, the mass-selective analyzer portion of a mass spectrometer system will simply be called a mass spectrometer. Ions introduced into a mass spectrometer are separated in a vacuum environment. Accordingly, it is necessary to prepare the sample undergoing analysis for introduction into this environment. This presents particular problems for high molecular weight compounds or other sample materials which are difficult to volatilize. While liquid chromatography is well suited to separate a liquid sample matrix into its constituent components, it is difficult to introduce the output of a liquid chromatograph (LC) into the vacuum environment of a mass spectrometer. One technique that has been used for this purpose is the electrospray method. The present invention is directed to improvements in the apparatus used to perform the electrospray technique.

The "electrospray" or "electrospray ionization" technique is used to produce gas-phase ions from a liquid sample matrix to permit introduction of the sample into a mass spectrometer. It is thus useful for providing an interface between a liquid chromatograph and a mass spectrometer. In the electrospray method, the liquid sample to be analyzed is pumped through a capillary tube or needle. A potential difference (of for example, three to four thousand volts) is established between the tip of the electrospray needle and an opposing wall, capillary entrance, or similar structure. The needle can be at an elevated potential and the opposing structure can then be grounded; or the needle can be at ground potential and the opposing structure can be at the elevated potential (and of opposite sign to the first case). The stream of liquid issuing from the needle tip is broken up into highly charged droplets by the electric field, forming the electrospray. An inert drying gas, such as dry nitrogen gas (for example) may also be introduced through a surrounding capillary to enhance nebulization (droplet formation) of the fluid stream.

The electrospray droplets consisting of sample compounds in a carrier liquid, are electrically charged by the electrical potential as they exit the capillary needle. The charged droplets are transported in an electric field and injected into the mass spectrometer, which is maintained at a high vacuum. Through the combined effects of a drying gas and vacuum the carrier liquid in the droplets starts to evaporate giving rise to smaller, increasingly unstable droplets from which surface ions are liberated into the vacuum for analysis. The desolvated ions pass through sample cone and skimmer lenses, and after focusing by a RF lens, into the high vacuum region of the mass-spectrometer, where they are separated according to mass and detected by an appropriate detector (e.g., a photo-multiplier tube).

Although the electrospray method is very useful for analyzing high molecular weight dissolved samples, it does have some limitations. For example, commercially available electrospray devices utilizing only electrospray nebulization to form the spray are practically limited to liquid flow rates of 20–30 microliters/min, depending on the solvent composition. Higher liquid flow rates result in unstable and inefficient ionization of the dissolved sample. Since the electrospray needle is typically connected to a liquid chromatograph, this acts as a limitation on the flow from the chromatograph.

One method of improving the performance of electrospray devices at higher liquid flow rates is to utilize a pneumatically assisted electrospray needle. One such device is formed from two concentric, stainless steel capillary tubes. In such a device the sample containing liquid flows through the inner tube and a nebulizing gas flows through the annular space between the two tubes. In one example of such a device, the inner diameter of the inner stainless steel capillary tube is approximately 0.1 mm, and its outer diameter is approximately 0.2 mm. The inner diameter of the outer tube is approximately 0.25 mm, leaving an annular space between the two tubes of thickness 0.025 mm. The inner tube is formed from a conductive material and has a high potential applied across it, to cause the electrospray ionization.

Figure 1A:
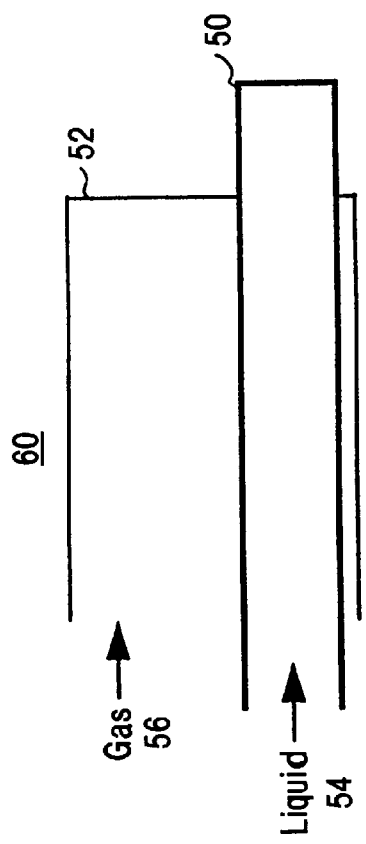

However, the described device has several disadvantages. At high liquid flow rates into this type of electrospray needle, larger size charged and uncharged liquid droplets are formed that can degrade the performance of the mass spectrometer if allowed to enter the spectrometer. In addition, it is difficult to align the two tubes coaxially, so that the tubes are concentric and the annular space between them is uniform. In practice, the inner tube will often contact the wall of the outer tube, as shown in FIGS. 1A and 1B, which are a schematic side view (1A) and end view (1B) showing the relative positions of the inner 50 and outer tubes 52 of a prior art electrospray needle 60. As indicated in the figures, a carrier liquid 54 containing the sample to be analyzed is pumped through inner tube 50, while a nebulizing gas 56 is made to flow through outer tube 52. Due to difficulties in establishing and maintaining the proper alignment between the two tubes, contact between them may occur, as shown in FIG. 1(B). Contact between the tubes results in a lower flow of nebulizing gas in the region of contact. The uneven gas flow will cause uneven gas pressures on the liquid exiting tube 50, and hence a nonuniform pneumatic nebulization of the liquid.

The asymmetry of the nebulizing gas flow arising from non-concentric alignment of the inner and outer tubes causes larger drop sizes, both when using pure pneumatic nebulization, or in combination with the effect of electrospray ionization. The asymmetric gas flow also causes a variation in the optimum location of the electrospray tube assembly with respect to the location of the entrance aperture into the mass spectrometer. This necessitates expensive and time consuming adjustments of the position of the spray assembly because of the variation in the spatial characteristics of the liquid spray.

The relatively high gas flow rates of the prior art device of FIG. 1 that are required to pneumatically assist the nebulization process during electrospray are also undesirable. This is because it is common to utilize an additional heated gas flowing in an opposite direction to the spray to increase the vaporization rate of the droplets and to prevent large droplets from entering the mass spectrometer. A large nebulizing gas flow will, to some extent, counteract the benefit of the drying gas by driving the large droplets into the sampling aperture. The introduction of large droplets into the mass spectrometer increases the noise generated during the mass-analysis.

What is desired is an apparatus which provides a method of producing ions using the electrospray technique which is capable of accommodating increased liquid flow rates. It is also desired that the apparatus provide a uniform flow of nebulizing gas and produce effective nebulization without the use of the high nebulizing gas flow rates found in prior art devices.

SUMMARY OF THE INVENTION

The present invention is directed to an apparatus for producing gas-phase ions from a sample compound in a carrier liquid. The electrospray needle (or capillary) of the present invention includes a central metal tube which carries the liquid containing the sample compound. The central tube is surrounded by a plurality of tubes which transport a nebulizing gas. The nebulizing gas tubes are placed symmetrically around the outside of the liquid containing tube. The nebulizer of the present invention produces a symmetric, non-annular gas flow which has variations in pressure around the circumference of the central tube. The pressure variations of the nebulizing gas flow produce additional shear forces on the liquid emerging from the central tube. This assists in forming a uniform electrospray of droplets from the liquid at lower nebulizing gas flow rates, thereby reducing the disadvantageous effects of the higher gas flow rates used in the art. The symmetric arrangement of the nebulizing gas tubes provides support for the central sample carrying tube, thereby reducing the alignment problems found in prior art devices, and enhancing uniformity of the electrospray.

BRIEF DESCRIPTION OF THE DRAWINGS

FIGS. 1A and 1B are a schematic side view (1A) and end view (1B) showing the relative positions of the inner and outer tubes of a prior art electrospray needle.

FIGS. 2A and 2B are a schematic side view (2A) and end view (2B) showing the relative positions of the inner tube and outer tubes of a first embodiment of the pneumatically assisted electrospray needle of the present invention.

FIGS. 3A and 3B are a schematic side view (3A) and end view (3B) showing the relative positions of the inner tube and outer tubes of a second embodiment of the pneumatically assisted electrospray needle of the present invention.

FIGS. 4A and 4B are a schematic side view (4A) and end view (4B) showing the relative positions of the inner tube and outer tubes of a third embodiment of the pneumatically assisted electrospray needle of the present invention.

FIGS. 5A and 5B are a schematic side view (5A) and end view (5B) showing the relative positions of the inner tube and outer tubes of a fourth embodiment of the pneumatically assisted electrospray needle of the present invention.

FIGS. 6A and 6B are a schematic side view (6A) and end view (6B) showing the relative positions of the inner tube and outer tubes of a fifth embodiment of the pneumatically assisted electrospray needle of the present invention.

FIG. 7 is a photograph showing the operation of a prior art pneumatically assisted nebulizing electrospray needle.

FIG. 8 is a photograph showing the apparatus of FIG. 7 for the case of a nebulizing gas flow rate lowered to 1270 ml/min.

FIG. 9 is a photograph showing the apparatus of FIG. 7 for the case of a nebulizing gas flow rate lowered to 640 ml/min.

FIG. 10 is a photograph showing the result for the same conditions as in FIG. 9, but with +4 kilovolts applied to the spray assembly, to create charged droplets by the electrospray process.

FIG. 11 is a photograph showing the operation of an electrospray apparatus constructed according to the present invention, having a central tube with six nebulizing gas tubes symmetrically disposed around the central tube.

FIG. 12 is a photograph showing the mist of small droplets that were continuously formed when 4 kilovolts was applied across the inventive electrospray apparatus of FIG. 11.

FIG. 13 is a photograph showing the pneumatic nebulization obtained by the apparatus of FIG. 11 with a nebulizing gas flow rate of 410 ml/min.

FIG. 14 is a photograph showing the mist of charged droplets formed when 4 kilovolts was applied to the inventive apparatus of FIG. 11 under the same conditions as in FIG. 13.

FIG. 15 is a photograph showing the droplets formed by the apparatus of FIG. 11 for the case of a nebulizing gas flow of 190 ml/min. and an applied voltage of 4 kilovolts.

FIGS. 16–18 are photographs showing the results of using the apparatus of FIG. 11 for sample liquid flow rates of 50 microliters/min with an applied voltage of 4 kilovolts, and with nebulizing gas flow rates of 690, 410, and 190 ml/min., respectively.

DETAILED DESCRIPTION OF THE INVENTION

The present invention is an electrospray needle which may be used in situations of relatively high sample liquid flow rates. The invention is therefore well suited for use as an interface between a liquid chromatograph and a mass spectrometer to permit mass spectrographic analysis of sample compounds separated by the chromatograph. The invention produces a pneumatically assisted electrospray with a lower nebulizing gas flow rate than that used for prior art devices, such as that shown in FIG. 1. This provides a more efficient means of producing the electrospray, while reducing the system noise resulting from the introduction of large drops into the mass spectrometer. The inventive design is also “self-aligning” in the sense that the central sample carrying tube is maintained in proper position relative to the nebulizing gas tubes by the symmetric arrangement of the nebulizing gas tubes around the central tube.

FIGS. 2A and 2B are a schematic side view (2A) and end view (2B) showing the relative positions of the inner tube and outer tubes of a first embodiment of the pneumatically assisted electrospray needle 100 of the present invention. The inventive electrospray needle includes a central metal tube 102 which contains a sample in an appropriate carrier liquid 106, such as that obtained from the output of a liquid chromatograph. Central tube 102 is surrounded by a plurality of tubes 104 used to transport a nebulizing gas 108. Outer tubes 104 are symmetrically arranged around the outside of inner tube 102. Outer tubes 104 provide a means for aligning tube 102 relative to tubes 104 and maintaining a desired flow of nebulizing gas 108 circumferentially around liquid 106. This reduces (and in an ideal case, eliminates) the time and effort which otherwise might be required to maintain alignment of the nebulizing gas and sample tubes.

A properly aligned, prior art concentric tube nebulizer of the type shown in FIG. 1 produces a uniform annular gas flow and therefore, a uniform gas pressure on the liquid emerging from the inner tube. This results in a constant shear force being applied to the sample carrying liquid around the circumference of the liquid stream emerging from the inner tube. In contrast, the nebulizer of the present invention produces a symmetric, non-annular gas flow having a pressure which cyclically varies around the circumference of the inner tube. This increases the shear forces applied to the sample liquid at symmetric positions around the emerging liquid stream. The inventive electrospray device thus assists in reducing the number and size of large droplets formed by the electrospray, while permitting a reduction in the nebulizing gas flow rate required for operation as compared to the prior art device.

The present invention produces a plurality of gas jets, disposed around central conducting tube 102 to pneumatically assist the electrospray ionization process. The non-annular nebulizing gas flow resulting from the present invention produces pressure variations around central conducting tube 102 which act to pneumatically assist electrospray ionization. The nebulizing gas flow produced by the invention forms alternating regions of high and low gas pressure on the liquid emerging from the central tube. This applies additional shear forces on the liquid, enhancing droplet formation at the relatively high liquid flow rates typical of the output of a liquid chromatograph. The present invention produces an electrospray of liquid droplets at a lower nebulizing gas flow rate than devices found in the art, thereby mitigating the undesirable effect of a high nebulizing gas flow rate on the effectiveness of a drying gas used to evaporate solvent from the charged ions.

Alternate embodiments of the present invention are shown in FIGS. 3 to 6. In the embodiment shown in FIGS. 3(A) and 3(B), central tube 102 is located inside of another concentric tube 10. This permits central tube 102 to be independently adjusted to vary its end position and distance from the surrounding nebulizer tubes. Another embodiment is shown in FIGS. 4(A) and 4(B), in which nebulizing gas carrying tubes 104 are positioned (angled) so that the nebulizing gas jets emerging from the tubes are directed to a location along the central axis of symmetry of the device. In the embodiment shown in FIGS. 5(A) and 5(B), the shape of the gas channels (i.e., the nebulizing gas carrying tubes) surrounding the central tube differs from that shown in the previous embodiments. Gas channels 105 shown in FIG. 5 may be made by crimping or swaging a concentrically arranged outer tube, by broaching the inside surface of the outer tube, or by electro-forming the outer tube over a suitably shaped form. As shown in FIG. 5, the gas channels of the present invention need not be circular in cross section, and can be a shape that is conveniently produced by one of the fabrication techniques mentioned, or another suitable technique.

The gas channels for carrying the nebulizing gas in the various embodiments disclosed herein need not be electrically conductive, since only the inner tube is required for the electrospray process. The embodiment in FIG. 3, for example, could be fabricated by forming the channels from a bundle of glass tubes that are drawn and fused together to the desired inside diameter. The glass bundle could then be sliced off in sections of the desired length and a metal tube inserted through the central tube to form the structure shown in FIGS. 3(A) and 3(B).

Figure 2B:
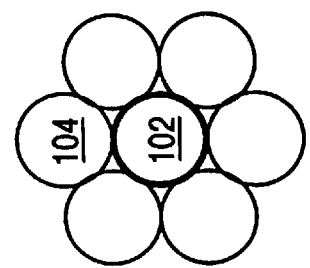
Figure 2A:
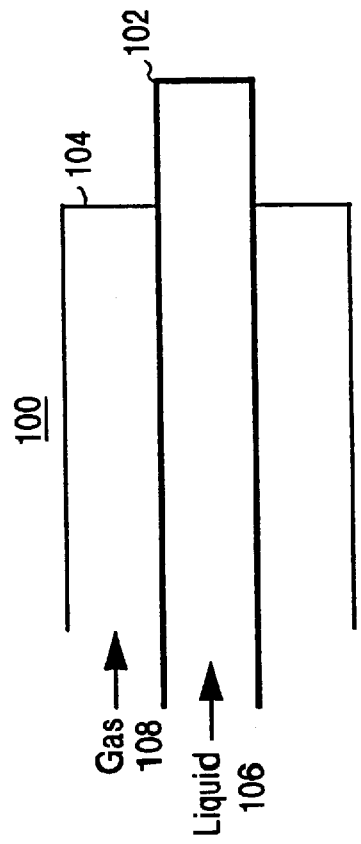
Figure 3B:
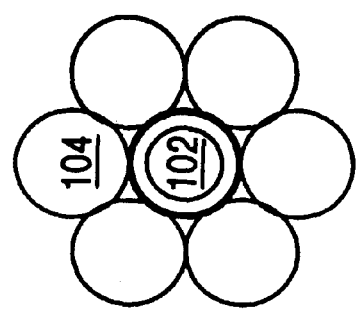
Figure 3A:
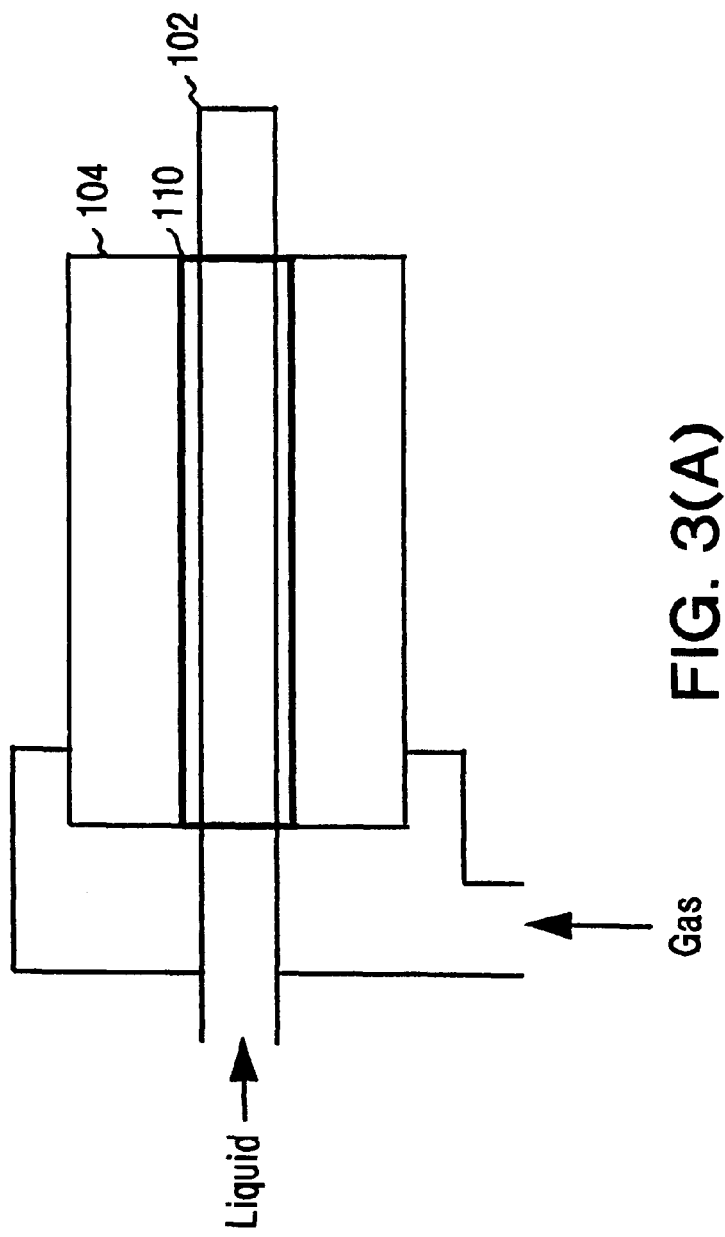
Figure 6B:
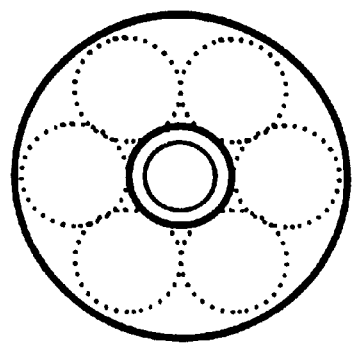
Figure 6A:
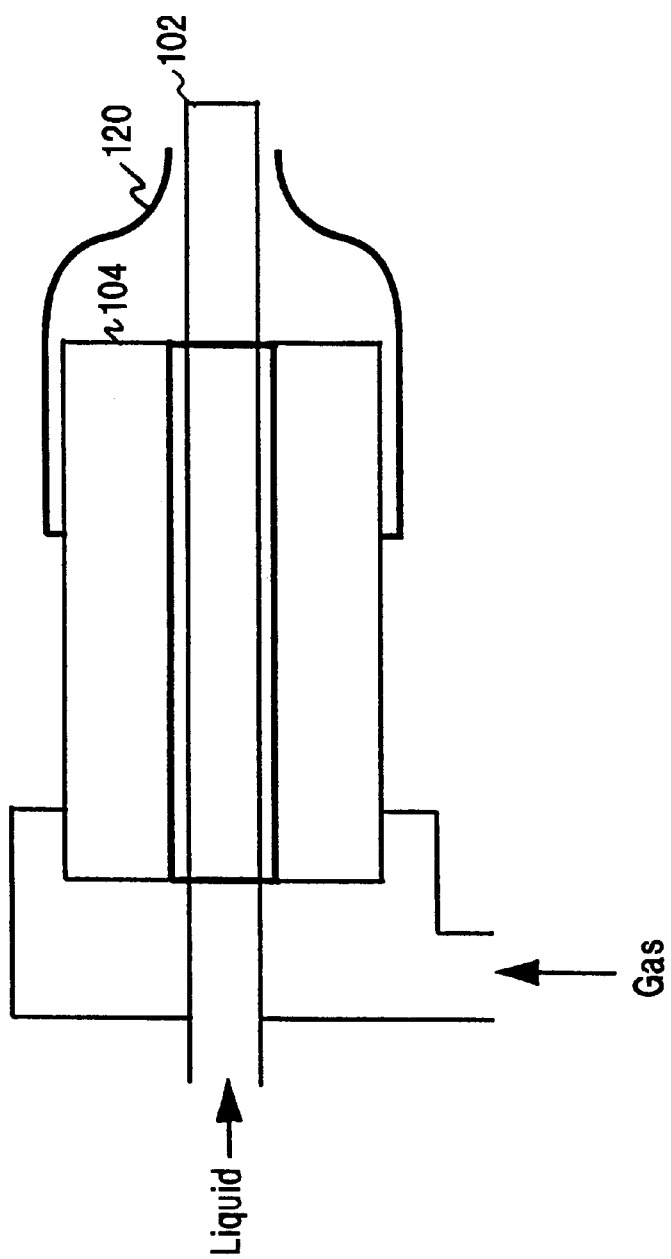

The embodiment of the present invention shown in FIGS. 6(A) and 6(B) is based on the structure shown in FIG. 2 or 3, but with an additional tube 120 placed around the outer tubes and necked down around the inner tube. Outermost tube 120 will force the nebulizing gas to merge again into a uniform annular flow. Outer tube 120 is registered on the plurality of tubes 104 surrounding inner tube 102, with tubes 104 supplying the gas flow to the annular region between inner 102 and outermost 120 tubes. This embodiment of the invention provides an improved device having a true annular gas flow, as opposed to the prior art device of FIG. 1 which does not exhibit such behavior. An alternate embodiment could utilize gas channels that are formed with a helix angle about the central tube, to impart a tangential flow component to the gas flow, with respect to the central liquid tube. This would impart additional shear forces to the flow in a direction transverse to the electric field. Such an embodiment could be formed, for example, from the embodiment of FIG. 3 wherein the outer tubes are twisted around sufficiently that the flow out of their ends forms an angle of approximately five to twenty degrees with respect to the longitudinal axis of the central tube.

Although multiple embodiments of the present invention have been described, one or another of them may be preferred in certain circumstances or under specific operating conditions. The embodiment of FIG. 2 may be preferred due to its simplicity. The embodiment of FIG. 3 has the advantage of permitting adjustment of the distance between the end of the central tube and the ends of the surrounding tubes, to allow optimization of this distance as a function of liquid flow rates. However, it does introduce the added complexity of requiring a mechanism to adjust the central tube. The embodiment of FIG. 4 has the advantage of focusing the nebulizing gas jets to a point, such as to the tip of the Raleigh cone where the liquid droplets are formed, but with the added complexity of requiring a mechanism to adjust the central tube so that the focal point is correct for different liquid flow rates. The embodiment of FIG. 5 has the advantage of simplicity of fabrication since the gas conduit structure can be formed by broaching, electroforming, or molding an non-metallic material, followed by pressing the central tube into the structure. This embodiment has the disadvantage of creating more turbulence in the corners of the gas conduits. The embodiment of FIG. 6 provides an improved method of providing a true annular gas flow.

Advantages of the present invention over the prior art are believed to include: (1) the ability to provide a device for pneumatically assisted electrospray capable of use with high sample liquid flow rates; (2) production of a symmetric gas flow with cyclical variation in pressure around the circumference of the inner tube, thereby supplying additional shear forces on the emerging liquid from the central tube as a result of forming regions on the liquid with alternating high and low pressures; (3) formation of a symmetrical spray of liquid droplets at a lower nebulizing gas flow rate and linear velocity than prior art devices; and (4) an electrospray device which can be used with a liquid chromatograph and which will maintain proper alignment between the central sample carrying tube and the surrounding nebulizing gas tubes without requiring adjustments which interrupt the mass spectroscopic analysis.

Figure 7:
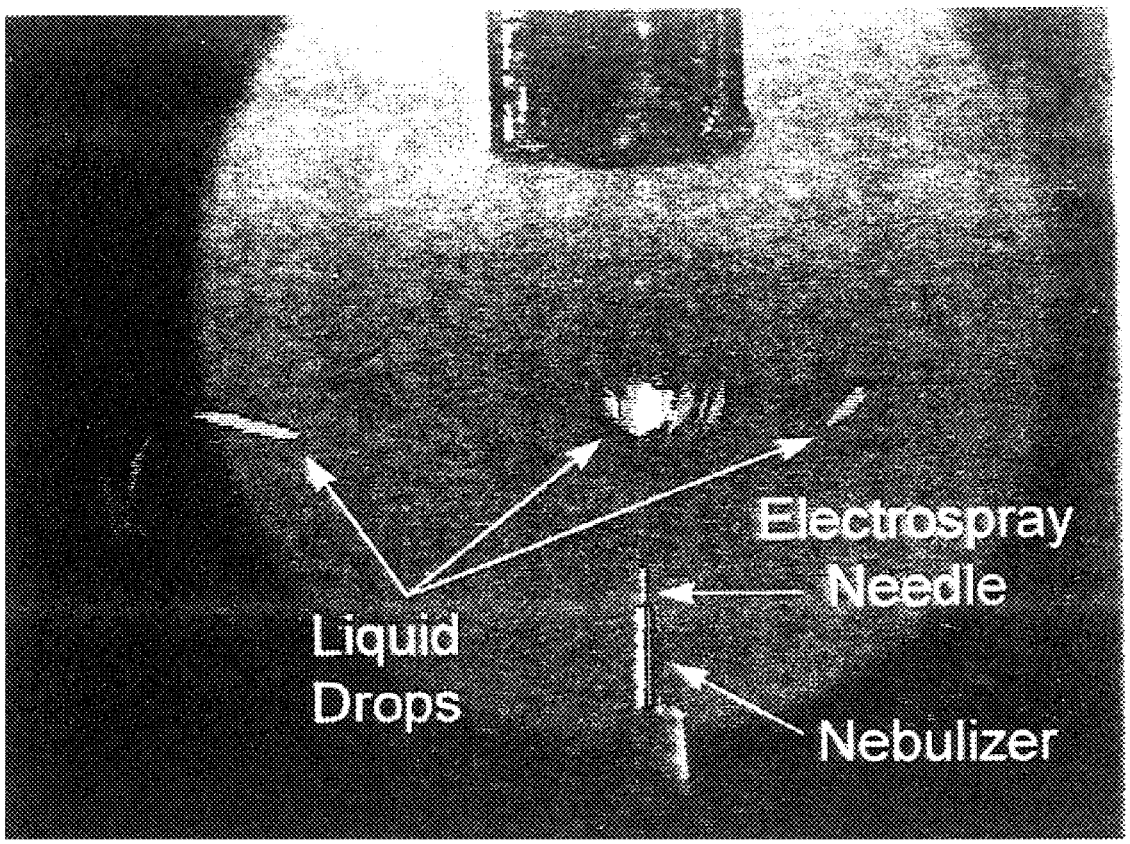

FIG. 7 is a photograph showing the operation of a prior art pneumatically assisted nebulizing electrospray needle constructed according to the dimensions described by Henion et. al. in U.S. Pat. No. 4,861,988, issued Aug. 29, 1989 (referred to as a "Concentric Tube Nebulizer" in the figures). The central tube has an inner diameter of 0.004" and an outer diameter of 0.008", and the outer tube has an inner diameter of 0.010" and an outer diameter of 0.018". The end of the central tube is displaced from the end of the outer tube by 0.040". In FIG. 7, the region between the end of the electrospray tube (the inner tube) and the opposing grounded surface is illuminated by a Helium/Neon laser to make the droplets visible. With a nebulizing gas flow rate of 1,870 ml/min., large droplets which are formed by pneumatic nebulization can be observed. The sample liquid flow rate through the central tube is 200 microliters/min. The sample material being analyzed is Ultramark 1621, obtained from PCR Inc., Gainesville, Fla. The compound is a fluorinated phosphazene, dissolved in a carrier of 50/50 acetonitrile/methanol. In the photograph of FIG. 7, no potential is established across the spray assembly.

Figure 8:
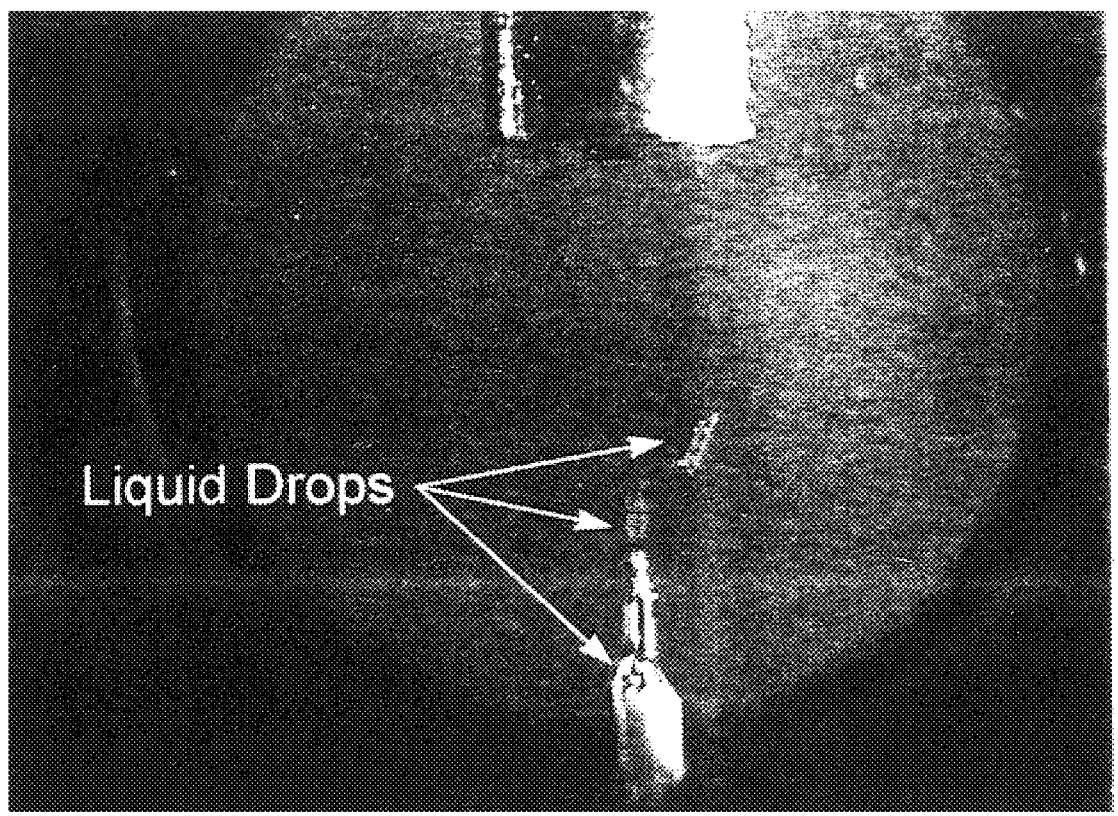

FIG. 8 is a photograph showing the apparatus of FIG. 7 for the case of a nebulizing gas flow rate lowered to 1,270 ml/min. Large drops of liquid were observed to accumulate at the end of the central tube, which then grew to a larger size and burst into smaller droplets. Some of the liquid was observed to be flowing backwards, along the outside of the inner tube, near the region where the two tubes were in contact (i.e. in the region where the two tubes contacted).

Figure 9:
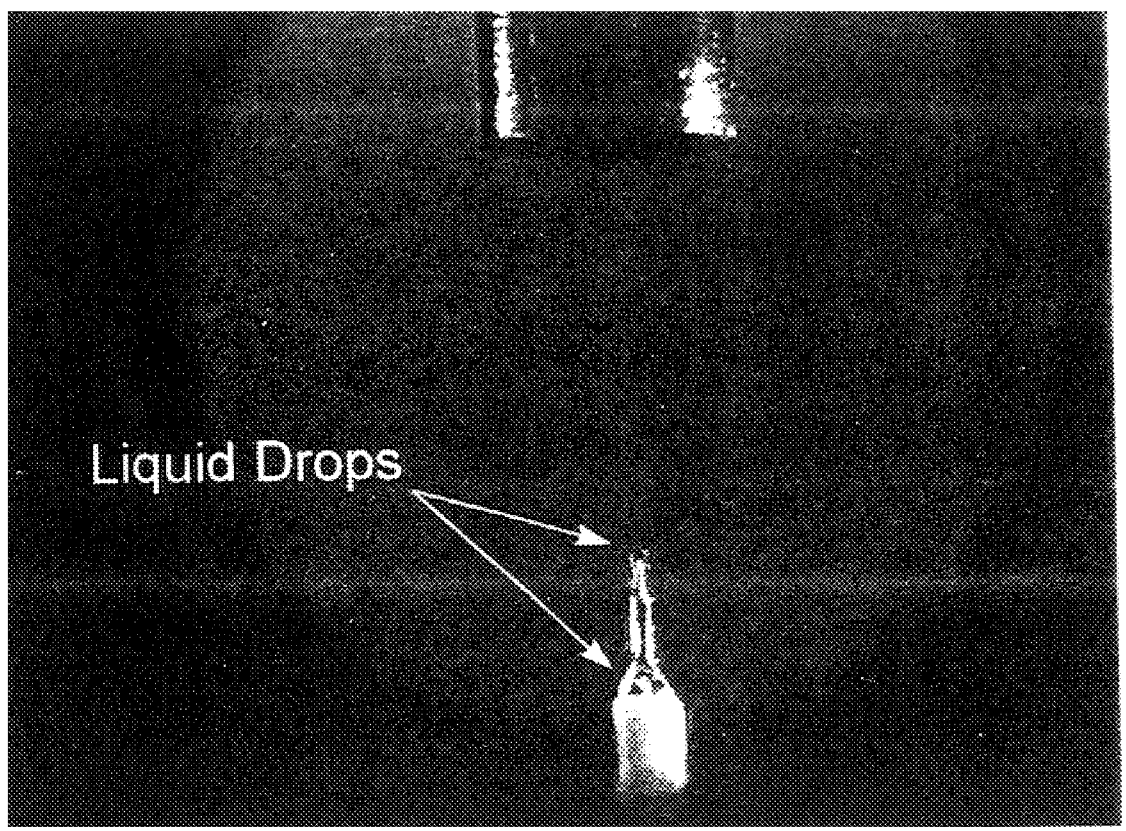

FIG. 9 is a photograph showing the apparatus of FIG. 7 for the case of a nebulizing gas flow rate lowered to 640 ml/min. At this gas flow rate the liquid accumulates at the end of the inner tube and flows backwards. From the figure, it appears that no nebulization occurs (or at least ineffective nebulization occurs).

Figure 10:
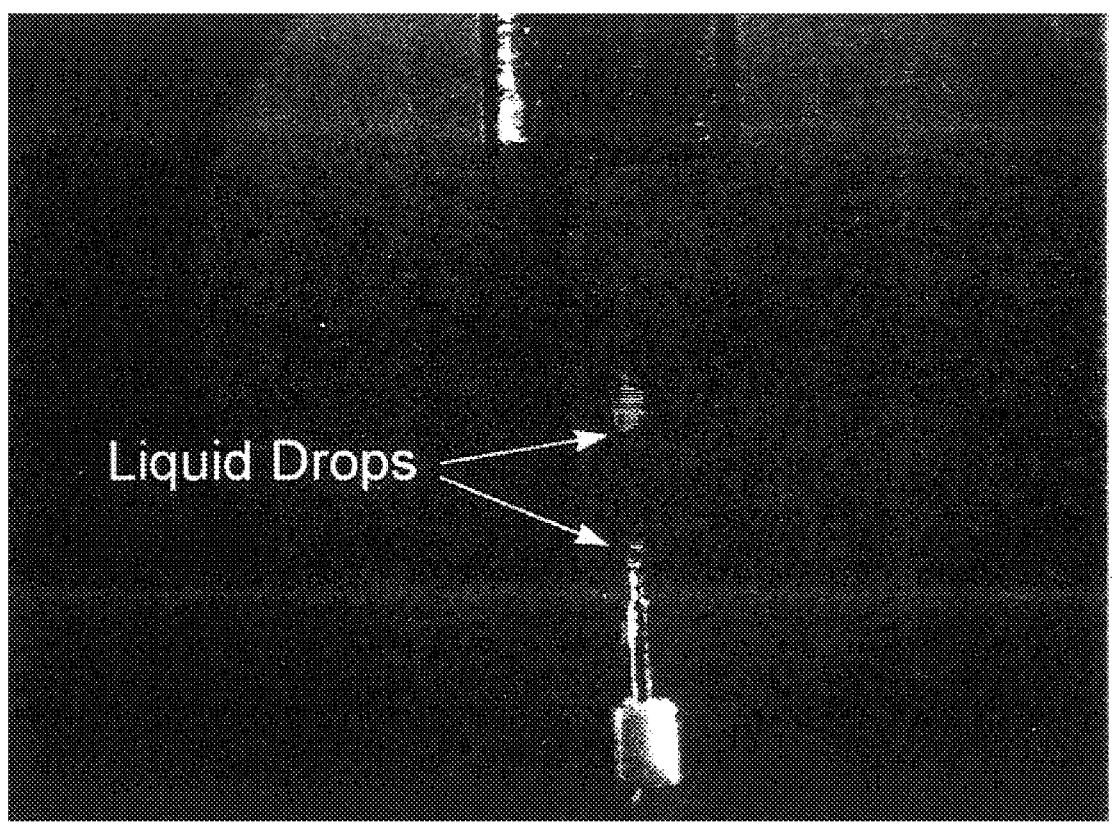

FIG. 10 is a photograph showing the result for the same conditions as in FIG. 9, but with +4 kilovolts applied to the spray assembly, to create charged droplets by the electrospray process. In this case the liquid was observed to accumulate at the end of the inner tube, grow to a large size, and then burst into smaller droplets. Such erratic formation of charged droplets results in undesired noise and inaccuracy in the mass spectrometer output signal.

Figure 11:
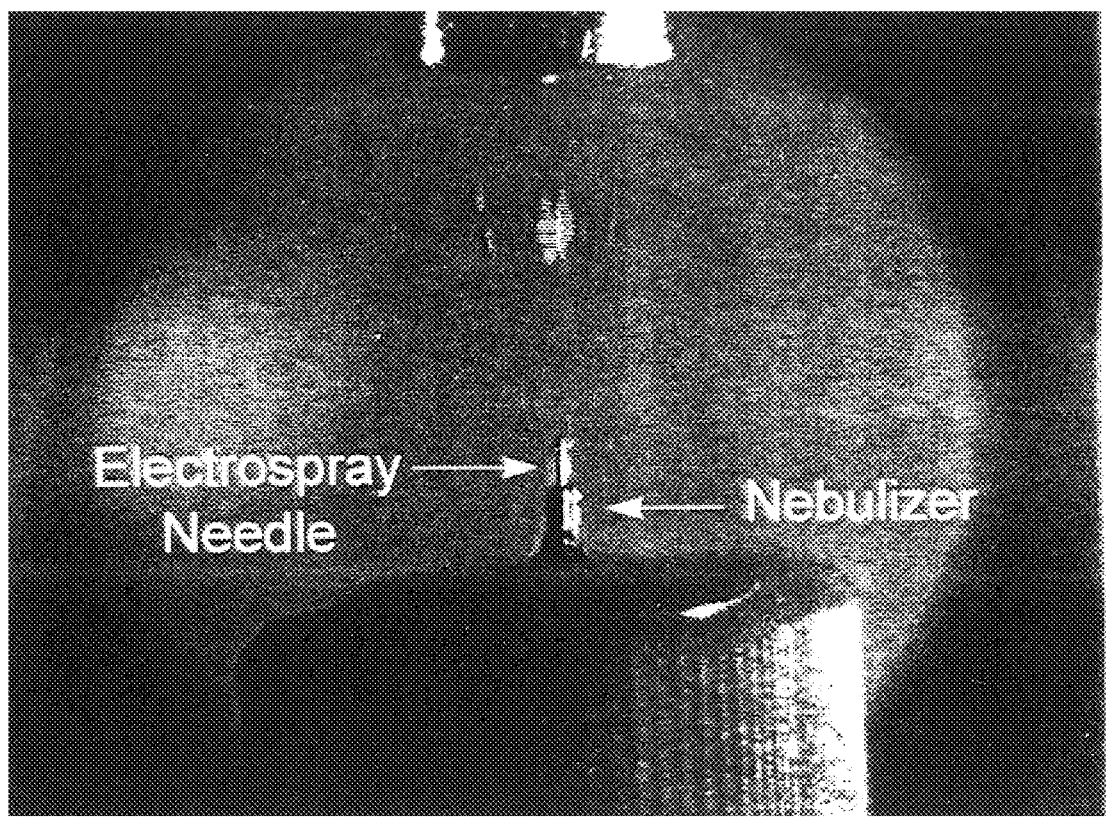

FIG. 11 is a photograph showing the operation of an electrospray apparatus constructed according to the present invention, having a central tube of inner diameter 0.004" and an outer diameter of 0.009", with six nebulizing gas tubes, of the same dimensions, symmetrically disposed around the central tube. The end of the central tube is displaced 0.040" from the ends of the outer tubes. In contrast to the observed performance of the prior art device shown in FIGS. 7–10, the apparatus of the present invention is capable of pneumatically nebulizing the 200 microliters/min. of sample liquid flow with a nebulizing gas flow of only 690 ml/min. This should be contrasted with the performance of the prior art shown in FIG. 9 (showing the operation of the prior art concentric nebulizer at a liquid flow rate of 640 ml/min.). The symmetrical spray of small droplets shown in FIG. 11 occurred in the absence of a potential being applied across the apparatus, with the other conditions being the same as for FIG. 9.

Figure 12:
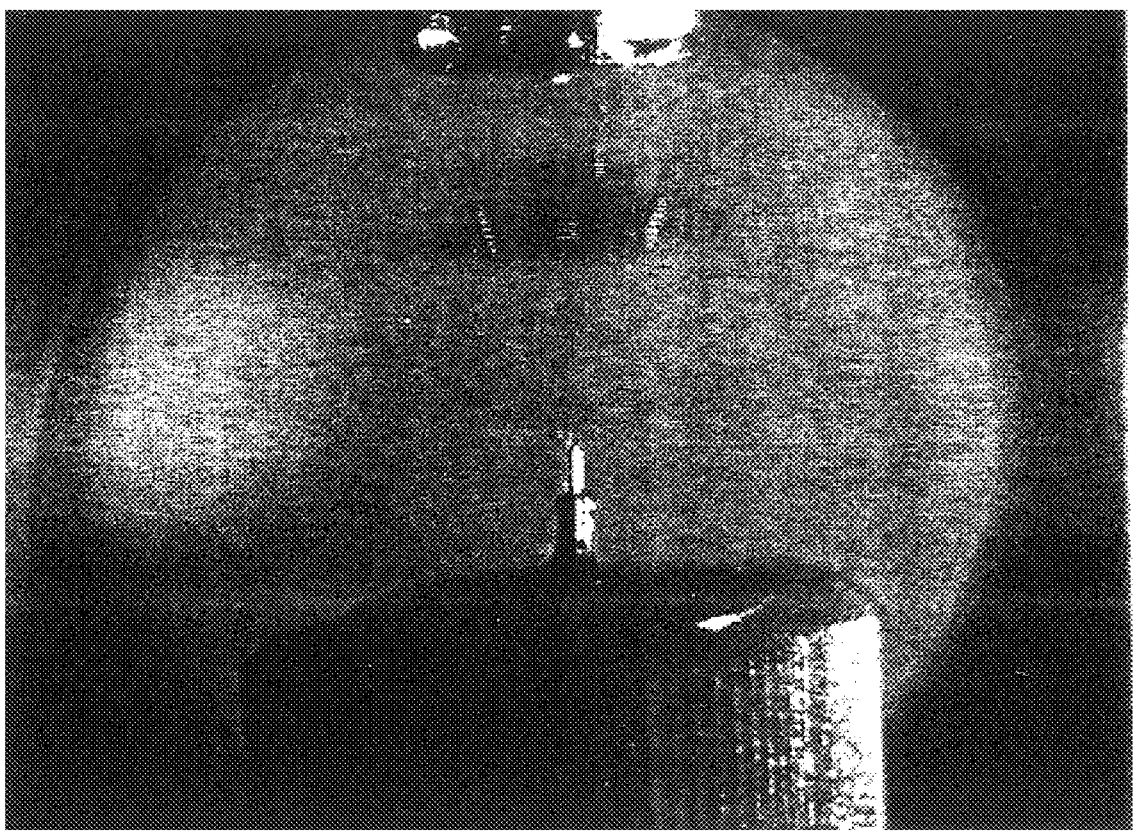
Figure 13:
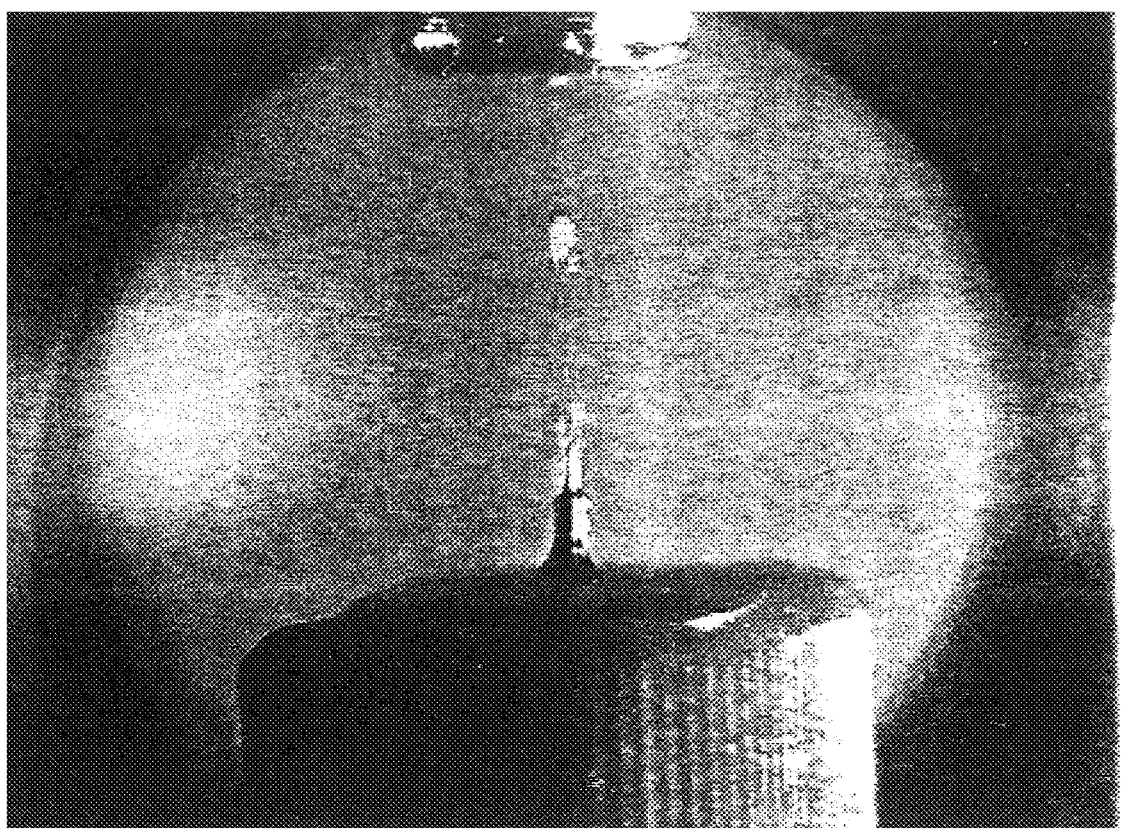
Figure 14:
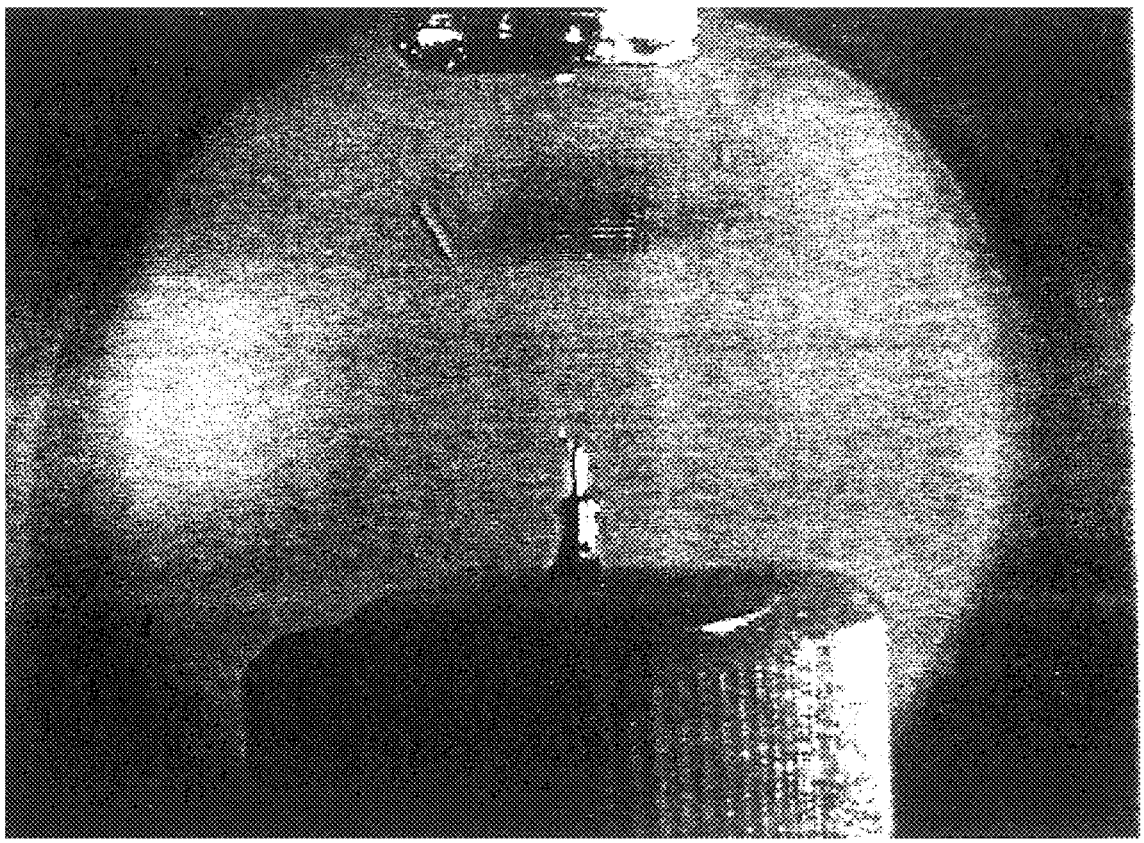
Figure 15:
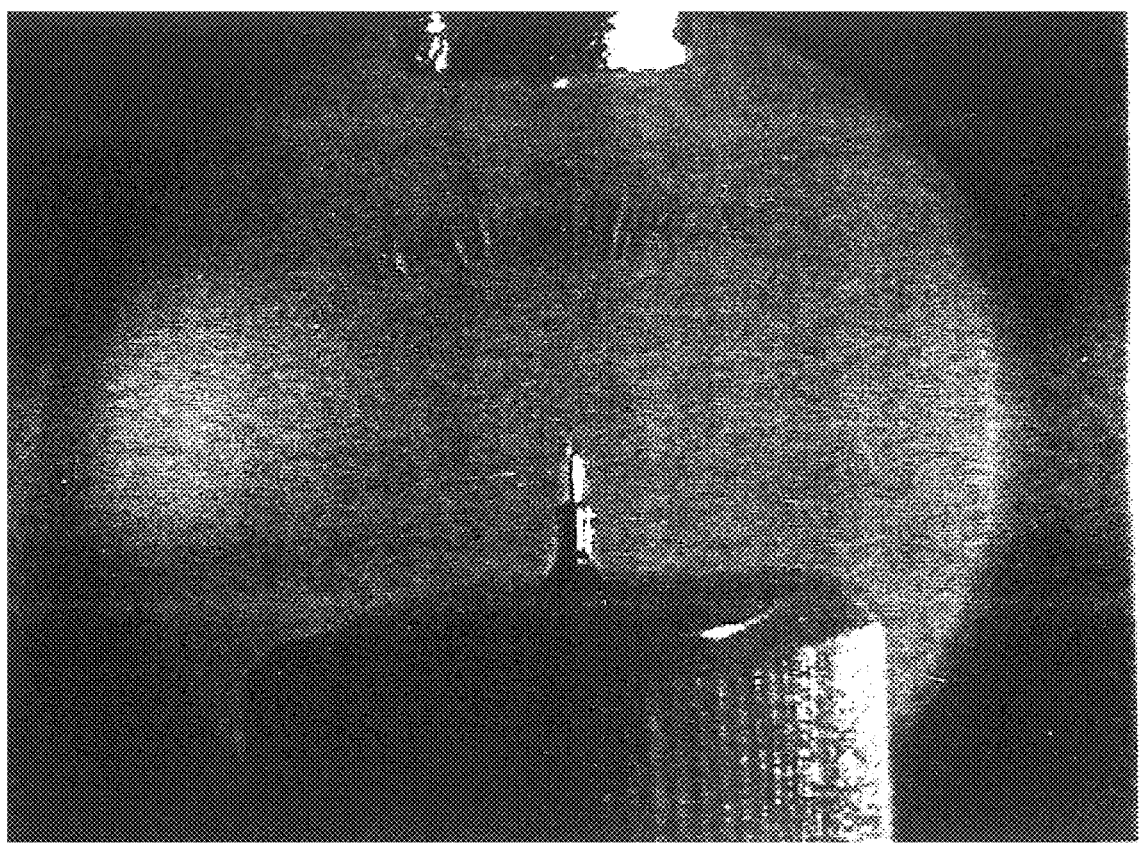
Figure 16:
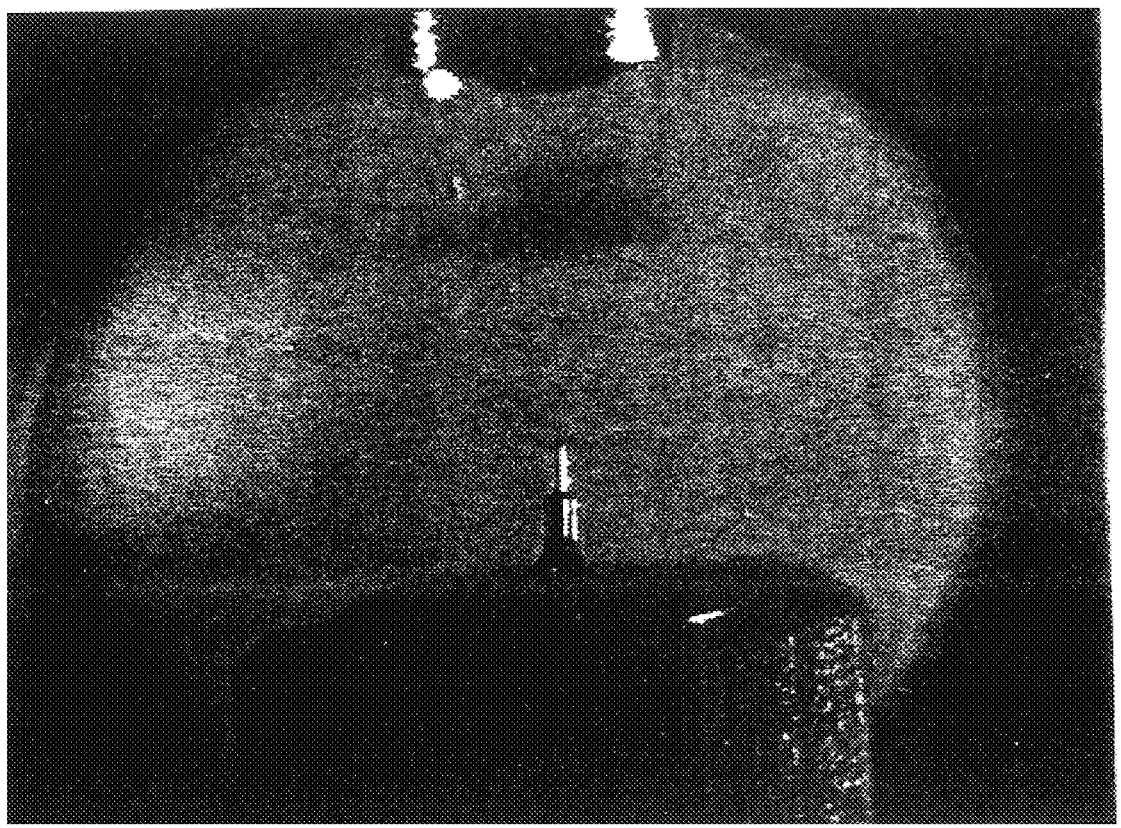
Figure 17:
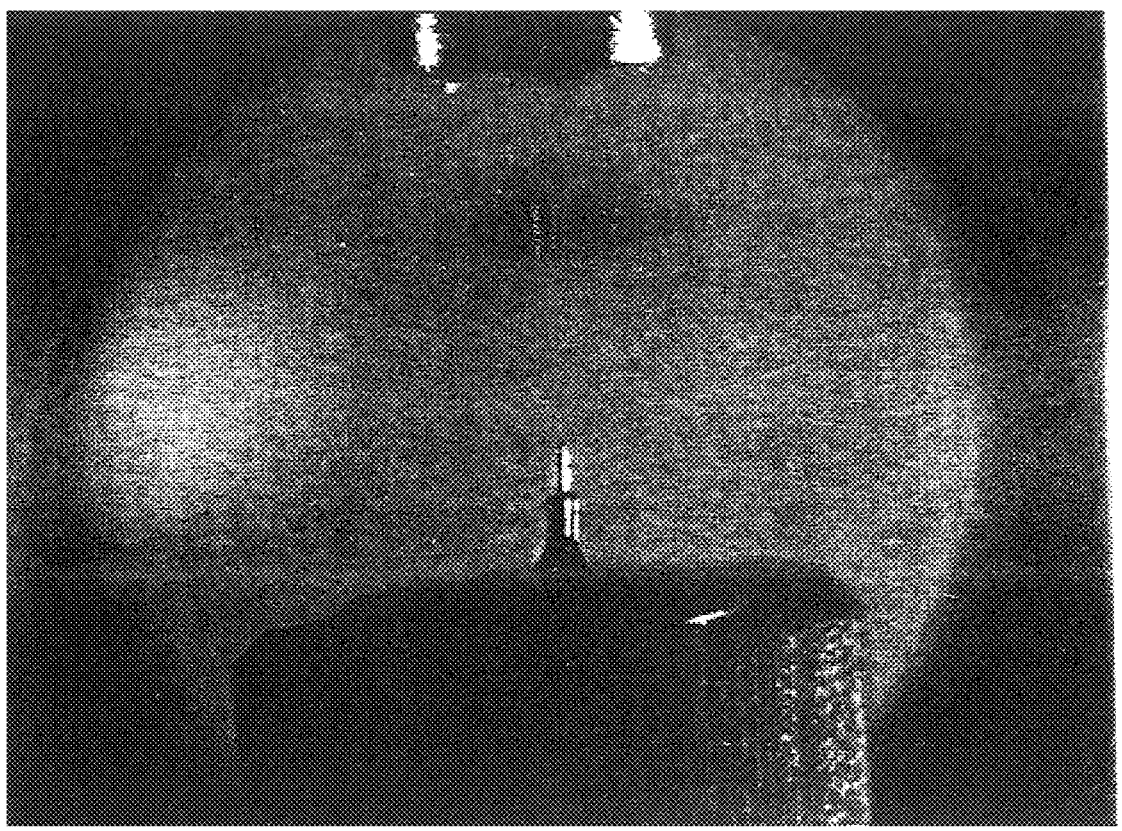
Figure 18:
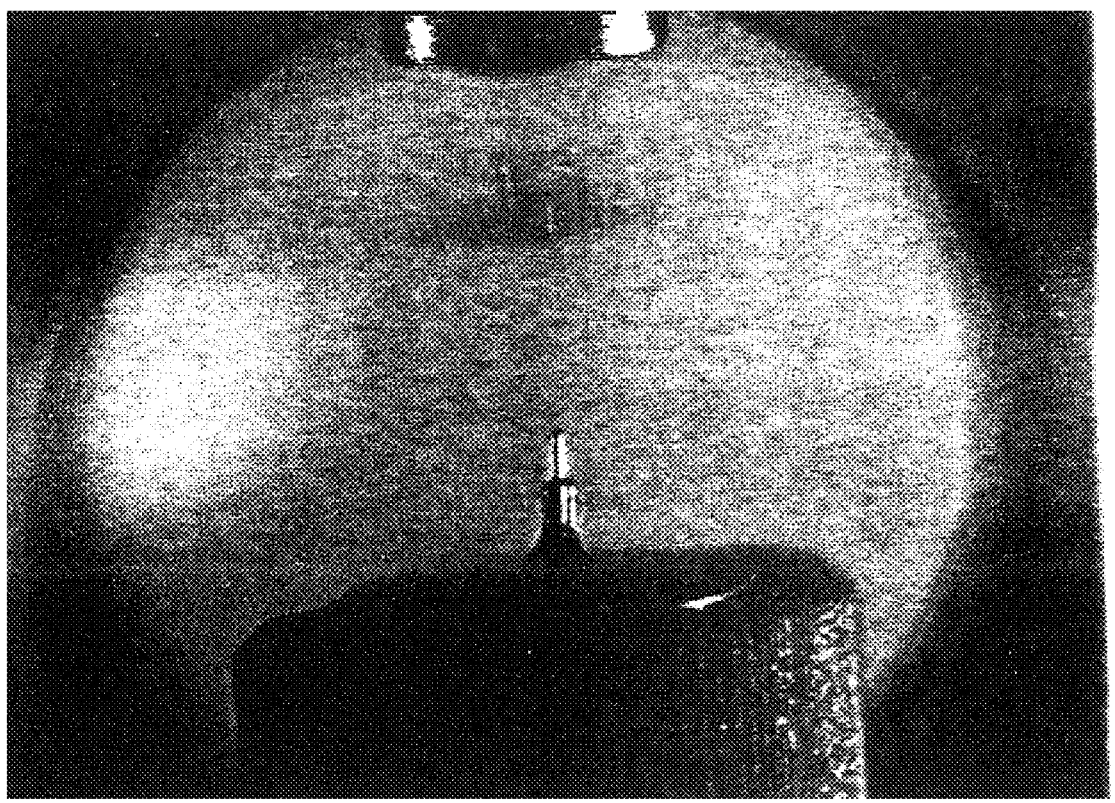

FIG. 12 is a photograph showing the fine mist of very small droplets that were continuously formed when 4 kilovolts was applied across the inventive electrospray apparatus of FIG. 11. FIG. 13 is a photograph showing the pneumatic nebulization obtained by the apparatus of FIG. 11 with a nebulizing gas flow rate of 410 ml/min. Although the nebulization is more erratic than in FIG. 12, no liquid was observed to flow in the direction counter to the gas flow, as was observed with the prior art device. FIG. 14 is a photograph showing the fine mist of charged droplets formed when 4 kilovolts was applied across the inventive apparatus under the same conditions as in FIG. 13. FIG. 15 is a photograph showing the droplets formed by the apparatus of FIG. 11 for the case of a gas flow of 190 ml/min. and an applied voltage of 4 kilovolts. FIGS. 16–18 are photographs showing the results of using the apparatus of FIG. 11 for sample liquid flow rates of 50 microliters/min with an applied voltage of 4 kilovolts, and with nebulizing gas flow rates of 690, 410, and 190 ml/min., respectively.

A preferred material for the central tube in the inventive device is a conductive material that is compatible with the liquid solutions that are flowing through it. The pH of the liquids can vary from 2–12 (acidic to basic), so the material (s) should be selected to be compatible with the solution characteristics. The central tube may be glass or fused silica that is coated with a conductive material, or a metal such as stainless steel. The outer tubes may be any material that is compatible with the surrounding chemical environment. This is because these tubes may be in contact with the droplets blown back onto them by the counter current drying gas. Thus, their needed resistance to chemical attack will affect their composition.

With regard to the dimensions of the inventive structures, this will depend to some extent on the liquid flow rate range that the device needs to operate over. As the liquid flow rate decreases, so too should the central tube diameter (although note that reducing the liquid flow rate also reduces the need for gas assisted nebulization). Conversely, as the liquid flow rate increases, the tube diameters should increase. The dimensions described previously for an embodiment of the present invention are suitable for liquid flow rates of 10–1000 milliliters/min.

A pneumatically assisted electrospray apparatus which overcomes many of the disadvantages of prior art devices has been described. The inventive apparatus is self-aligning thereby effectively eliminating the need to interrupt the analysis process to re-align a pair of concentric tubes. The shear forces produced by the nebulizing gas tubes assist in producing effective nebulization at reduced nebulizing gas flow rates compared to prior art devices, permitting the invention to be efficiently used at the higher sample liquid flow rates typical of the output of a liquid chromatograph.

The terms and expressions which have been employed herein are used as terms of description and not of limitation, and there is no intention in the use of such terms and expressions of excluding equivalents of the features shown and described, or portions thereof, it being recognized that various modifications are possible within the scope of the invention claimed.

What is claimed is:

1. An electrospray apparatus for forming a spray of charged particles from a sample carrying liquid, comprising:
   a central conduit for transporting the sample carrying liquid containing a sample carrying liquid discharge port; and
   a plurality of conduits for transporting a nebulizing gas arranged exterior to and symmetrically around the central tube,
   each of said plurality of conduits comprising a nebulizing gas output port, said nebulizing gas output ports producing azimuthally alternating regions of high and low nebulizing gas pressure distributed about said discharge port;

said discharge port axially disposed in respect of said output ports in said azimuthally alternating regions.

2. The electrospray apparatus of claim 1, further comprising:

means for establishing a potential difference between an outlet end of the central conduit and an opposing surface.

3. The electrospray apparatus of claim 1, wherein the central conduit has a circular cross-section.

4. The electrospray apparatus of claim 1, where in the conduits for transporting the nebulizing gas have a circular cross-section.

5. The electrospray apparatus of claim 1, wherein the central conduit and conduits for transporting the nebulizing gas have a circular cross-section, and further, wherein the central and nebulizing gas conduits have substantially the same diameter.

6. The electrospray apparatus of claim 1, further comprising:

a support conduit arranged exterior to and coaxially with the central conduit, positioned between the central conduit and the conduits for transporting the nebulizing gas and sized to permit the central conduit to be moved axially with respect to the support conduit.

7. The electrospray apparatus of claim 1, wherein the conduits for transporting the nebulizing gas are arranged to be substantially parallel to the central conduit.

8. The electrospray apparatus of claim 1, where in the conduits for transporting the nebulizing gas are arranged at an angle with respect to the central conduit.

9. The method of forming a spray of charged particles from a sample carrying liquid, comprising the steps of a) transporting said sample carrying liquid generally along a central axis to a selected point on said central axis, b) transporting a nebulizing gas independently along a plurality of paths spaced from said central axis, and allowing said nebulizing gas from each said plurality of paths to expand at substantially the same axial coordinate whereby gas pressure is exerted radially and azimuthally on said sample carrying liquid whereby said radially directed pressure varies around said sample carrying liquid in the plane transverse to said central axis in the neighborhood of said axial coordinate.

10. The method of claim 8 further comprising establish a potential difference between said sample carrying liquid and the neighborhood thereof.

11. The method of forming a spray of charged particles from a sample carrying liquid, comprising the steps of a) transporting said sample carrying liquid generally along a central axis to a selected point on said control axis, b) transporting a nebulizing gas independently along a plurality of paths spaced from said central axis, and allowing said nebulizing gas from each said plurality of paths to expand at substantially the same axial coordinate whereby gas pressure is exerted radially and azimuthally on said sample carrying liquid whereby said radially directed pressure varies around said sample carrying liquid in the plane transverse to said central axis in the neighborhood of said axial coordinate, c) directing each of said plurality of paths to intersect said central axis at a selected point along said central axis.

12. The method of forming a spray of charged particles from a sample carrying liquid, comprising the steps of a) transporting said sample carrying liquid at a first flow rate generally along a central axis to a selected point on said central axis, b) transporting a nebulizing gas independently at a second flow rate along a plurality of paths spaced from said central axis, and allowing said nebulizing gas from each said plurality of paths to expand at substantially the same axial coordinate whereby gas pressure is exerted radially and azimuthally on said sample carrying liquid whereby said radially directed pressure varies around said sample carrying liquid in the plane transverse to said central axis in the neighborhood of said axial coordinate, c) adjusting said selected point on said central axis with respect to said same axial coordinate to optimize said selected point for said flow rates.

* * * * *